United States Patent [19]
Grubbs

[11] Patent Number: 4,869,669
[45] Date of Patent: Sep. 26, 1989

[54] ORAL CHOCK FOR SETTING DENTAL PROTHESES

[76] Inventor: Kenneth Grubbs, 101 Dover St., Monroe, Ga. 30655

[21] Appl. No.: 177,486

[22] Filed: Apr. 1, 1988

[51] Int. Cl.$^4$ ............................................. A61C 5/00
[52] U.S. Cl. ...................................... 433/140; 433/71
[58] Field of Search ............................... 433/140, 71

[56] References Cited

U.S. PATENT DOCUMENTS

| | | | |
|---|---|---|---|
| 2,103,115 | 12/1937 | Mizzy et al. | 433/140 |
| 2,594,830 | 4/1962 | Wade | 433/71 |
| 3,722,101 | 3/1975 | Via | 433/140 |

Primary Examiner—Robert Peshock
Attorney, Agent, or Firm—James B. Middleton

[57] ABSTRACT

An oral chock exerts uniformly axial forces on dental prostheses to seat the prosthesis. The chock is preferably shaped like the dental arch, and wedge-shaped to align the surfaces of the chock with the occlusal surfaces of the teeth. The chock is large enough to receive the entire dental arch, so that one or a plurality of prostheses of any size or extent can be seated. The chock may be scored for separation into partial chocks, and the central posterior portion may be removed for palatal and lingual relief. The chock is formed of expanded plastic material having a frangible cellular structure for deformation of the chock so that the chock will exert uniformly distributed forces. Though deformable, the material has sufficient strength to seat the prostheses.

12 Claims, 1 Drawing Sheet

U.S. Patent    Sep. 26, 1989    4,869,669
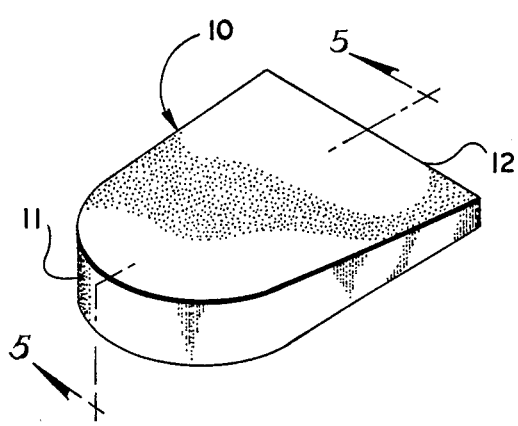
Fig_1
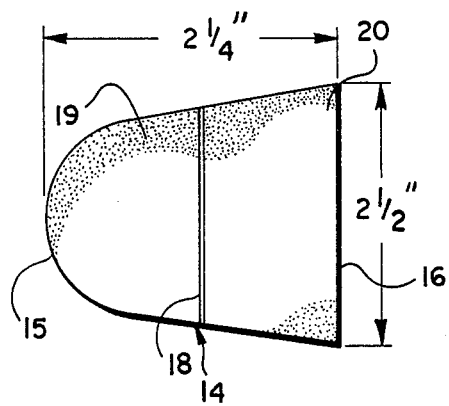
Fig_2
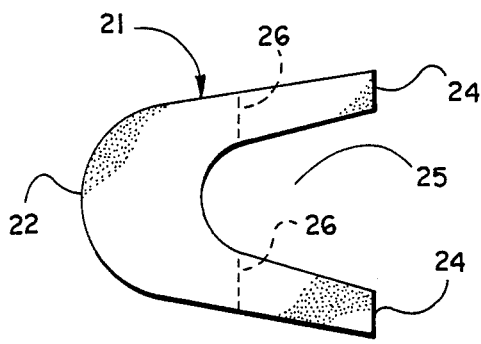
Fig_3
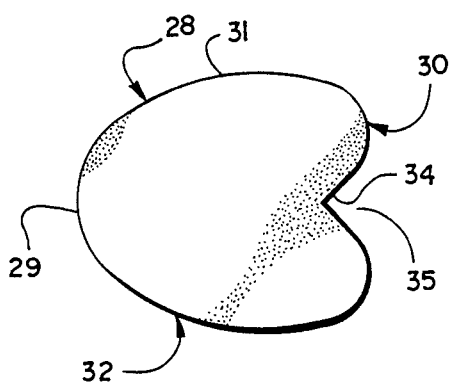
Fig_4
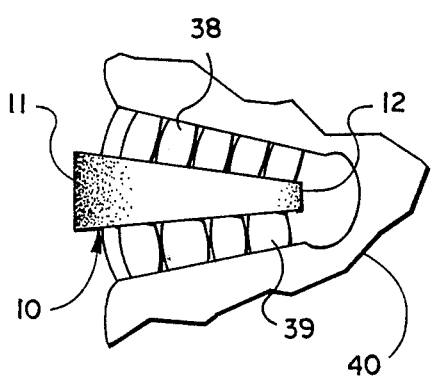
Fig_6
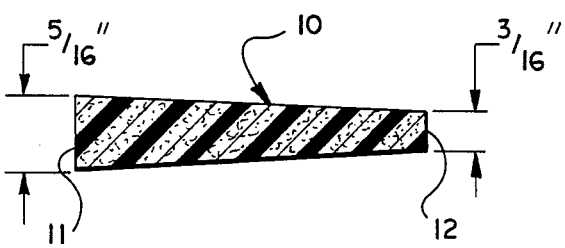
Fig_5

ORAL CHOCK FOR SETTING DENTAL PROTHESES

INFORMATION DISCLOSURE STATEMENT

It is very common in dentistry to place some form of prosthesis in or on a tooth, the general technique including the grinding away of a portion of the tooth and replacement of that portion with an appropriate prosthesis. The prostheses have usually been made of a gold alloy or the like, and more recently they have also been made of ceramic materials. Typically, the prosthesis is checked for proper fit, then receives a cement and is put into place in the tooth. It will be understood that considerable force may be required to seat the prosthesis properly for the final cementing in place. In order to seat the prosthesis, the usual technique is to place a chock between the patient's jaws and request that the patient bite hard on the chock. This pressure seats the prosthesis.

One difficulty with the prior art technique is that, in the event there is a single prosthesis on one side of the jaw, the patient's jaw meets uneven resistance, so the mandible tends to cant, thereby placing undue stress on the rather complex joint for the mandible. If a plurality of prostheses is to be seated at any given time, the dentist must normally place a plurality of individual chocks between the patient's teeth to engage the various appropriate teeth, then ask the patient to bite down. Placing these chocks, and holding all of the chocks in the appropriate position until the patient bites, can be somewhat tedious, and may require several tries before all of the chocks can be put into place at the same time. Further, there is currently no known technique for seating a full complement of teeth, or a roundhouse.

Further difficulties with the prior art chocks is that the prior art chocks are typically made of a completely unyielding material that will tend to be somewhat uncomfortable to the patient, and may not exert uniformly axial forces on the tooth. Alternatively, the chock may be made of an elastic material that offers an uncomfortable reactive force to the biting by the patient.

SUMMARY OF THE INVENTION

This invention relates generally to chocks and the like, and is more particularly concerned with a deformable material for use as a chock in setting dental prostheses.

The present invention provides a generally wedge-shaped, somewhat frangible, mouth chock having a shape substantially like the shape of the oral arch. If desired, the central posterior portion may be omitted to provide palatal and lingual relief. Also, the present invention may comprise a chock for the anterior portion only, or may comprise the posterior portion only. While the preferred embodiment of the invention includes a chock for the complete arch, the chock may be scored or otherwise separable to produce the partial chocks.

The chock of the present invention is formed of an expanded plastic material having a somewhat frangible cellular structure but with sufficient strength to provide the needed force to set prostheses such as crowns, inlays, on-lays, bridges and the like. Materials such as expanded polystyrene and expanded rigid polyurethane work quite well, materials having the stated characteristics are also within the scope of the present invention.

BRIEF DESCRIPTION OF THE DRAWINGS

These and other features and advantages of the present invention will become apparent from consideration of the following specification when taken in conjunction with the accompanying drawings in which:

FIG. 1 is a perspective view showing an oral chock made in accordance with the present invention;

FIG. 2 is a top plan view of a chock similar to that shown in FIG. 1, and showing a score-line for separating the full chock into two partial chocks;

FIG. 3 is a view similar to FIG. 2, but showing a posterior opening for palatal and lingual relieve;

FIG. 4 is a view similar to FIG. 3, but showing another embodiment of the invention;

FIG. 5 is a cross-sectional view taken substantially along the line 5—5 is FIG. 1; and, FIG. 6 is a side elevational view showing the chock of FIG. 1 in conjunction with a set of teeth.

DETAILED DESCRIPTION OF THE EMBODIMENTS

Referring now more particularly to the drawings, and to those embodiments of the invention here presented by way of illustration, FIG. 1 shows a chock generally designated at 10. The chock has a curved anterior end 11, and a generally straight posterior surface 12. It will be noted that the posterior end of the chock 10 is relatively thin, with the surfaces diverging towards the anterior end 11 to give the entire chock a wedge shape in side elevation. It will therefore be understood that the chock 10 is shaped very much as the conventional arch, and of course more than one size will be required. There is a considerable body of knowledge as to the standard arches, and those skilled in the art will readily determine the number of sizes, and the particular sizes, to be made.

Looking at FIG. 2 of the drawings, the chock is designated at 14, and the anterior end is designated at 15 while the posterior edge is designated at 16. Substantially centrally between the anterior apex and the posterior edge 16 there is a score-line designated at 18. A chock made in accordance with the present invention can be scored as along the line 18, and an anterior chock 19 can be separated from a posterior chock 20 in the event the partial chock is desired.

Using the arrangement shown in FIG. 2, it will be realized that the anterior chock 19 will cover the anterior portion of the arch and including the incisors, while the posterior chock 20 will cover both sides of the mouth.

A chock such as that shown in FIG. 1 of the drawings may sometimes offer sufficient discomfort to a patient that some relief must be had. The chock in FIG. 3 is designated at 21, and again has the end 22 and the posterior edge 24. In FIG. 3 it will be noted that the central posterior portion of the chock 21 is removed to provide an opening 25. It will be realized that the chock 21 therefore provides coverage of the full arch of the teeth, but the opening 25 provides for some relief of the patient's tongue, as well as of the rear palatal portion to prevent gagging and other discomfort.

The device shown in FIG. 3 also includes a broken line 26 which may be a score-line if desired. Thus, the device shown in FIG. 3 may be provided with a score line for separation of the anterior portion from the posterior portion; and, on separation, it will be noted that the posterior portion will comprise two separate chocks which may be used either unilaterally or bilaterally.

FIG. 4 of the drawings shows a somewhat different form of the device shown in FIG. 3, the chock in FIG. 4 being designated at 28. The chock 28 includes an anterior end 29 and a posterior edge generally designated at 30.

The anterior edge 29 is, as before, shaped to fit the conventional arch of the teeth. The sides 31 and 32 also extend rearwardly along the normal arch. At the posterior edge 30, the edge curves and turns inwardly forming a reentrant angle 34. This reentrant angle 34 then provides an opening 35 for the palatal and lingual relief as was discussed in conjunction with FIG. 3. The chock 28 shown in FIG. 4 of the drawings therefore provides a comparable result, but with a different shape that may be more aesthetically pleasing and have better stability in general handling.

FIG. 5 of the drawings is a longitudinal cross-sectional view of the chock 10 shown in FIG. 1 of the drawings, and is intended to show the relative sizes. Looking at FIGS. 2 and 5, it will be seen that some dimensions for the chock are shown. Those skilled in the art will readily understand that the specific dimensions will be quite variable, due somewhat to personal preference, and due to a large extent to the actual sizes of the dental arch. Nevertheless, by way of example it will be seen that the full length of the chock may be about 2¼inches or around 5½centimeters. The complete width at the posterior edge 12 or 16 might be about 2½inches, or about 6¼centimeters. The anterior edge can conveniently be around 5/16 inch, or around 8 millimeters thick, while the posterior edge 12 or 16 might be around 3/16 inch thick or about 5 millimeters. Again, it will be understood that these dimensions are by way of illustration only and are meant to be no way restrictive. These specific dimensions will vary to suit the individual applications.

Looking at FIG. 6 briefly, it will be seen that the chock designated at 10 is placed between the upper teeth generally designated at 38 and the lower teeth designated at 39. It will be understood that, when the teeth are opened, the mandible generally designated at 40 moves in a pivotal motion so that the teeth 38 and 39 do not remain parallel. It is for this reason that the chock 10 is formed in a wedge shape.

With the above description in mind, the further operation of the present invention should be understandable. The chock will be made of a somewhat frangible material such as an expanded polystyrene or an expanded, rigid, polyurethane. A polystyrene having a density in the range of 4 to 8 pounds per cubic foot has been found to be useful in practicing the present invention. The more preferred range is 5 to 7 pounds per cubic foot, and the most preferred density is 6 pounds per cubic foot. Polyurethanes in the same general range are useful in practicing the invention, but patients may find the urethanes to be somewhat objectionable as having a gritty texture.

It will be understood that the polystyrene, though expanded and crushable due to its frangible cellular structure, has considerable strength. In view of the preferred density of about 6 pounds per cubic foot, it will be realized that the material can be crushed to a certain extent, but then will provide sufficient resistance to further crushing that it will exert relatively large reactive forces. In view of this phenomenon, a patient can receive a chock such as the chock 10 between the upper and lower teeth 38 and 39, and the patient can bite down on the chock 10. The patient's teeth will sink into the chock 10, but the material will then offer sufficient resistance that the patient's teeth will not enter the material any further. In this process, it will be recognized that the forces exerted on the patient's teeth are substantially in line with the axes of the teeth themselves. As a result, when the dentist is attempting to seat a crown, in-lay or the like, the forces to seat the prosthesis will be substantially axial of the tooth so the forces will be balanced and the prosthesis will not be urged off center or otherwise have distorting forces exerted thereon.

The fact that the chock of the present invention provides balanced force is especially important in view of view of the current use of friable materials such as the ceramics that are now used extensively in dentistry. It will be understood that a complete chock, such as the one illustrated in FIG. 1, will provide uniform, axially directed forces on each tooth, and will also provide balanced forces throughout the dental arch. Thus, the chock of the present invention can seat a prosthesis of any size or extent without producing uneven forces that may fracture the unit.

In view of the strength of the materials contemplated for use in the present invention, a chock made in accordance with the present invention can also be used to seat a prosthesis such as a crown, in-lay or the like, even if there is no opposing tooth. The strength of the materials such as polystyrene or polyurethane is such that a gap of at least one tooth can be bridged by the material and still provide sufficient force to seat the prosthesis. It will of course be understood that a sufficiently long span of missing teeth will cause such distortion of the chock that insufficient force will be exerted.

It will therefore be understood that the embodiments of the present invention provide considerable versatility to allow a dentist to utilize his own preferred technique. The chock of the present invention can be used in the form shown in FIG. 1 for the full arch, and with maximum material. For some palatal and/or lingual relief, the embodiments shown in FIGS. 3 or 4 can be utilized, still providing pressure on the full dental arch. In the event the dentist prefers to use only an anterior or posterior chock, the chock shown in FIGS. 2 or 3 can be separated into anterior and posterior portions for appropriate use. Of course the arrangement shown in FIG. 2 would generally be preferred since the posterior portion 20 would remain unitary for easier placement. Nevertheless, if the patient is particularly subject to gagging, the lingual or palatal relief may be required, and the two separate pieces that would result from separating the chock 21 can be utilized.

It will of course be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

I claim:

1. An oral chock for engagement by at least two teeth of a plurality of teeth in an oral cavity for seating a prosthesis for at least one tooth, said chock being dimensioned for said engagement by at least two teeth, said chock being shaped like the dental arch and dimensioned for bilateral engagement by said plurality of teeth, and formed of a material having a frangible cellular structure so that said chock is partially deformable and exerts sufficient force to set the prosthesis.

2. An oral chock as claimed in claim 1, said chock having an anterior end shaped like the dental arch, and a length from anterior to posterior to engage the entire dental arch.

3. An oral chock as claimed in claim 2, said anterior end having a greater thickness than the posterior edge of said chock, so that said chock is wedge shaped.

4. An oral chock as claimed in claim 3, said chock defining a score line laterally thereof for facilitating selective separation of said chock into an anterior and a posterior portion.

5. An oral chock as claimed in claim 4, said chock defining a central posterior opening for providing lingual relief.

6. An oral chock as claimed in claim 1, said material having a density within the range of four to eight pounds per cubic foot.

7. An oral chock as claimed in claim 6, said density being within the range of five to seven pounds per cubic foot.

8. An oral chock as claimed in claim 7, said density being six pounds per cubit foot.

9. An oral chock as claimed in claim 6, said material being selected from the group consisting of expanded polystyrene and expanded rigid polyurethane.

10. A method for seating dental prostheses, said method including the steps of placing a chock between the jaws for bilateral contact and located to engage the prosthesis to be seated, said chock being formed of a deformable material, biting on said chock for providing indentations in said chock, and biting further with teeth in said indentations for providing seating forces axially of the tooth receiving the prosthesis.

11. A method as claimed in claim 11, characterized in that said step of placing a chock between the jaws includes placing a chock of sufficient dimensions for bilateral engagement with selectively at least the anterior and posterior portion of the dental arch.

12. A method as claimed in claim 11, characterized in that said step of placing a chock between the jaws includes placing a chock having sufficient dimensions for engaging the entire dental arch.

* * * * *